(12) United States Patent
Foussat (10) Patent No.: US 8,992,907 B2
(45) Date of Patent: Mar. 31, 2015

(54) COMPOSITIONS FOR TREATING AN INTESTINAL INFLAMMATORY CONDITION

(75) Inventor: Arnaud Foussat, Biot (FR)

(73) Assignee: Txcell, Valbonne (FR)

(*) Notice: Subject to any disclaimer, the term of this patent is extended or adjusted under 35 U.S.C. 154(b) by 686 days.

(21) Appl. No.: 12/744,697

(22) PCT Filed: Nov. 26, 2008

(86) PCT No.: PCT/EP2008/066263
§ 371 (c)(1),
(2), (4) Date: May 26, 2010

(87) PCT Pub. No.: WO2009/068575
PCT Pub. Date: Jun. 4, 2009

(65) Prior Publication Data
US 2010/0303780 A1    Dec. 2, 2010

Related U.S. Application Data

(60) Provisional application No. 60/990,013, filed on Nov. 26, 2007.

(30) Foreign Application Priority Data

Nov. 26, 2007 (EP) ..................................... 07301581

(51) Int. Cl.
*A01N 63/00* (2006.01)
*C12N 5/0783* (2010.01)
*A61K 35/28* (2006.01)
*A61K 35/12* (2006.01)

(52) U.S. Cl.
CPC ............ *C12N 5/0636* (2013.01); *A61K 35/28* (2013.01); *A61K 2035/122* (2013.01); *A61K 2035/124* (2013.01); *C12N 2501/23* (2013.01)
USPC ...................................................... 424/93.71

(58) Field of Classification Search
None
See application file for complete search history.

(56) References Cited

PUBLICATIONS

Foussat, A., et al. J. Immunol. 2003;171:5018-5026.*
Groux et al. Nature. 1997;389:737-742.*
120 Diseases, Bennett and De Burgh, eds. Bright Star Pubs.2007;pp. 166-169.*
Rumbo, M., et al. Clin. Exp. Immunol. 1998;112:453-458.*

* cited by examiner

*Primary Examiner* — Gerald R Ewoldt
(74) *Attorney, Agent, or Firm* — Young & Thompson (57) ABSTRACT

Compositions comprising human Tr1 cells directed to a food antigen from common human diet and methods for treating an intestinal inflammatory condition.

20 Claims, 8 Drawing Sheets

COMPOSITIONS FOR TREATING AN INTESTINAL INFLAMMATORY CONDITION

FIELD OF THE INVENTION

The present invention relates to the field of treatment of an intestinal inflammatory condition. The present invention relates in particular to methods for treating inflammatory bowel diseases and intestinal inflammation linked to food intolerance or allergy, using a medicament comprising human Tr1 cells directed against a food antigen from common human diet.

BACKGROUND

Intestinal inflammatory condition as used herein refers to inflammatory bowel disease and inflammation linked to food intolerance or allergy.

Inflammatory bowel disease (IBD) refers to a group of diseases including both Crohn's disease and ulcerative colitis. The two diseases are often grouped together due to their similar pathogenesis and clinical manifestations. In the absence of invasive imaging studies, it is not possible to distinguish the two diseases which are often considered as a single disease in a number of publications and studies. Definitive diagnosis of either disease requires imaging studies such as endoscopy (either sigmoidoscopy or colonoscopy), double contrast barium enema, and computed tomography (CT) scan; combined with laboratory tests including complete blood counts to detect elevated leukocyte levels, erythrocyte sedimentation rates and serum albumin concentration.

Both diseases are chronic, relapsing/remitting inflammatory diseases of the gastrointenstinal tract. The regions of the gastrointenstinal tract that are most often affected by Crohn's disease are the small intestine and large intestine, also called the colon, including the rectum; however, Crohn's disease can affect the entire gastrointenstinal tract from the mouth to the anus. There may be single or multiple patches of inflammation. Ulcerative colitis affects only the large intestine. Inflammation and ulceration in ulcerative colitis are limited to the mucosal and submucosal layers, two innermost layers of the four layers of the large intestine. The inflammation and ulceration in Crohn's disease can extend through all layers of the intestinal wall in both the small and large intestines. Common symptoms of the diseases include diarrhea, abdominal pain, rectal bleeding and weight loss. Complications of Crohn's disease include intestinal abscesses, fistula, abnormal passage leading from one portion of the intestine to another and permitting passage of fluids or secretions, and intestinal obstructions. Typically, the course of both diseases is intermittent, with disease exacerbations followed by periods of remission. However, ulcerative colitis may be a single event, or continuous with unrelenting symptoms.

Although there are many choices for therapeutic interventions in IBD, many have undesirable side effects that make them less than ideal for treatment of chronic disease. For mild ulcerative colitis, orally or topically (i.e. enema) delivered aminosalicylates are typically the first line of treatment. The aminosalicylate class consists of agents that contain 5-aminosalicyclic acid (5-ASA), is one of the oldest anti-inflammatory compounds employed in IBD. Used in high doses, 5-ASAs can induce remission in acute attacks. Although commonly used for maintenance therapy, 5-ASAs have not been demonstrated to be effective in maintaining remission. Commonly used 5-ASA formulations include sulfasalazine, oral and topical mesalamine, olsalazine and balsalazide. Various formulations are modified to provide available active drug to the site of interest (e.g. small or large intestine). Side effects are however not uncommon with 5-ASAs.

Corticosteroids are among the most effective agents for inducing remission in IBD attacks and are typically the second therapeutic option upon failure of treatment with 5-ASAs. The compounds are delivered first either orally or rectally, with or without concomitant administration of 5-ASAs. Upon failure of oral delivery, the compounds are administered intravenously. Ideally, corticosteroids are used for only a short course of treatment and tapered off upon remission of disease. Corticosteroids commonly used for the treatment of IBD include prednisone, budesonide and hydrocortisone. The use of corticosteroids is limited by the number of severe and significant side effects associated with their use. Common side effects of short term use include insomnia, night sweats, mood changes and altered glucose metabolism. Prolonged maintenance therapy is typically reserved only for severe, refractory cases. Prolonged therapy can lead to adrenal atrophy, whereas abrupt cessation can cause adrenal insufficiency, hypotension, and even death. Other side effects include acne, abnormal fat deposition, excessive hair growth and osteoporosis. In Crohn's disease, corticosteroids can thwart the healing of fistula, exacerbating the disease state.

Individuals responding to oral or rectal corticosteroids are often placed on a maintenance dose of 5-ASA. However, some physicians provide no pharmacological interventions during periods of remission.

Individuals who require therapy with intravenous corticosteroids are typically maintained on an immunosuppressive agent such as 6-mercaptopurine and/or azathioprine, in combination with a 5-ASA. Parenteral nutrition is typically considered with such severe disease. When the patient does not respond to the above therapies, the immunosuppressant cyclosporine may be administered in an attempt to avoid surgery to remove the section of diseased intestine. Immunosuppressant interventions are not without undesirable side effects. 6-Mercaptopurine and azathioprine can cause fever, rash, nausea and headache, with more severe side effects including leucopenia, pancreatitis, severe infections and bone marrow suppression. Cyclosporine can have more severe side effects including paresthesias (abnormal sensations like burning or tingling), excessive hair growth, hypertension, tremor, renal insufficiency, headache and opportunistic infections.

Antibiotics, typically ciprofloxacin or metronidazole, are used as add on therapies to 5-ASA or corticosteroids, especially with patients with fistulizing or colonic disease. As with all of the other therapies, there are side effects of long term treatment with antibiotics.

Infliximab and adalimumab are currently the pharmacotherapy of last resort in inflammatory bowel diseases. Infliximab is a chimeric monoclonal antibody composed of 75% human and 25% mouse protein, whereas adalimumab is full humanized antibody. Infliximab and adalimumab are inhibitors of tumor necrosis factor-alpha (TNF-α), a potent inflammatory cytokine. The drug acts as a sink by binding both soluble and membrane bound TNF-α. By inhibiting an activator high in the inflammatory cascade, a number of inflammatory pathways can be inhibited. The drug is administered intravenously first for treatment and subsequently as a maintenance drug every eight weeks as indicated on the product label. However, as it is a biological agent, an immune response can limit utility of the drug.

Therefore, immunosuppressive agents are typically given in conjunction with infliximab maintenance therapy. As with all other therapies for inflammatory bowel diseases, there are substantial side effects of infliximab. TNF-α plays an important role in the eradication of neoplastic cells; therefore, its suppression can lead to opportunistic infections, malignancies and other complications, especially as a long term strategy.

Surgical interventions are a method of treatment of inflammatory bowel diseases, not a cure. Due to the chronic nature of IBD and the relatively early age of onset, multiple surgeries can be required over the lifetime of patients who are not responsive to pharmacological interventions. Removal of short portions of the intestine is possible without substantial side effects. However, removal of larger or multiple segments of the intestine can result in short bowel syndrome in which individuals are unable to absorb nutrients. Removal of portions of the large intestine can result in the need for colostomy or other further surgical procedures. Therefore, surgery is not a preferred method of treatment of inflammatory bowel diseases. Surgical interventions for the treatment of inflammatory bowel diseases can result in further disease. Upon complete removal of the colon, an ileal pouch may be constructed from the small intestine by the surgeon to allow removal of feces through the anus rather than requiring a permanent ostomy. Pouchitis is a non-specific inflammation of the ileal pouch which typically occurs within the first two years after reconstruction. Symptoms include steadily increasing stool frequency that may be accompanied by incontinence, bleeding, fever and/or a feeling of urgency. Of those who have ulcerative colitis, approximately 20 to 30 percent experience at least one episode. Antibiotics can be sufficient to treat pouchitis; however, other more aggressive therapies similar to those used in IBD are required.

Among the recent new therapeutic approaches for treating inflammatory bowel diseases, WO2007/027132 discloses a method for treating said diseases, comprising the administration of regulatory CD4+CD25+ T cells collected from sentinel nodes of the patient and expanded in vitro.

Another type of intestinal inflammatory condition is due to food intolerance or allergy. Humans rather frequently suffer from more or less severe allergic or intolerance reactions after consumption of dietary proteins. The prevalence of food allergy or intolerance is approximately 1-2% in adults and 6-8% in children. Food allergy or intolerance is mainly associated with a limited range of foodstuffs, mainly peanuts, tree nuts, hen's eggs, cow's milk, wheat (gluten), soybeans, fish and shellfish.

To date, no effective treatment of food allergy or intolerance is available. Most allergic or intolerant individuals adapt to their situation and avoid intake of foodstuffs to which they are allergic or intolerant. Therapies involving drugs, such as antihistamines, decongestants, or steroids, are available but only combat the symptoms of intolerance or an allergic reaction. They do not prevent that future exposure to the allergen or dietary proteins causes new allergenic reactions or new intolerance.

In the present invention, the Applicant thus aims to provide a treatment for intestinal inflammatory condition based on the use of Tr1 cells, which are different from regulatory CD4+ CD25+ T cells.

Groux et al (Nature 1997, 389:737-742) described that transfer of antigen (ovalbumin)-specific Tr1 cells prevents intestinal bowel disease induced by pathogenic CD4+ CD45RB$^{high}$ T cells in mice, only when said Tr1 cells are stimulated in vivo by the antigen (in this case, by feeding the mice with ovalbumin). In addition, Foussat et al. (Journal of Immunology 2003, 171:5018-5026) described that co-administration of antigen (ovalbumin)-specific Tr1 cells and the antigen (ovalbumin in the drinking water) cures ongoing inflammatory bowel disease in mice. Co-administration of the antigen was a necessity for the Tr1 cells to be efficient.

According to the invention, the inventors aim to provide a treatment for an intestinal inflammatory condition in a subject in need thereof, said treatment being based on the unique administration of Tr1 cells directed against a food antigen from common human diet. In particular, the inventors surprisingly found that said Tr1 cells directed against a food antigen from common human diet do not need to be co-administrated with the food antigen from common human diet to be efficient.

SUMMARY OF THE INVENTION

The present invention is directed to a composition comprising at least one human Tr1 cell population directed against a food antigen from common human diet.

Said food antigen from common human diet is preferably selected from the group comprising bovine antigens, Ca-binding S1OO, alpha-lactalbumin, lactoglobulins such as beta-lactoglobulin, bovine serum albumin, caseins, atlantic salmon antigens, chicken antigens, ovalbumin, Ag22, conalbumin, lysozyme or chicken serum albumin, shrimp antigens, wheat antigens, celery antigens, carrot antigens, apple antigens, apple lipid transfer protein, apple profilin, pear antigens, isoflavone reductase, avocado antigens, apricot antigens, peach antigens, soybean antigens, peanuts, ovalbumin, fragments, variants and mixtures thereof. Preferably, said food antigen is ovalbumin, casein, beta-lactoglobulin, soya protein, gliadin, peanuts, fragments, variants and mixtures thereof.

Another object of the present invention is to provide a medicament or a pharmaceutical composition comprising the composition of the invention.

The present invention relates also to a method for treating an intestinal inflammatory condition in a subject in need thereof, comprising administering to said subject an effective amount of the medicament or the pharmaceutical composition of the invention.

In a preferred embodiment of the invention, said method is for treating an inflammatory bowel disease. In one embodiment of the invention, said inflammatory bowel disease is Crohn's disease. In another embodiment of the invention, said inflammatory bowel disease is ulcerative colitis.

In another preferred embodiment of the invention, said method is for treating intestinal inflammation linked to food allergy or intolerance. In one embodiment, said food intolerance is celiac disease. In another embodiment, said food allergy is milk protein allergy. In another embodiment, said food allergy is peanut allergy. In another embodiment, said food allergy is ovalbumin allergy.

In a preferred embodiment, the medicament or the pharmaceutical composition to be administered to a subject in need thereof comprises human Tr1 cells autologous to the cells of said subject.

In another embodiment of the present invention, the method for treating an intestinal inflammatory condition in a subject in need thereof comprises the administration to said subject of an effective amount of the medicament or the pharmaceutical composition of the invention in combination with another therapeutic agent used for treating intestinal inflammatory conditions.

BRIEF DESCRIPTION OF THE DRAWINGS

(A) IL-4, IL-10 and IFN-γ production by mouse anti-fish proteins Tr1 cells. (B) IL-4, IL-10 and IFN-γ production by mouse anti-soy proteins Tr1 cells.

FIG. 3: Cytokine and expansion profiles of ovalbumin specific Tr1 clones from healthy donors. Example of 2 different clones. (A) Expansion yields of ovalbumin Tr1 clones were evaluated by cell count once a week upon weekly stimulation with artificial *drosophila* derived feeder cells. (B) Tr1 clones were assessed for their specificity for ovalbumin after specific activation during two days in the presence of antigen presenting cells. Ovalbumin-specific production of IL-10 was measured in supernatants by ELISA on three clones given as examples of the quality control testing. Results are expressed as the delta of IL-10 production between stimulating conditions with or without ovalbumin. (C) The Tr1 specific cytokine production profile was evaluated by ELISA on supernatant of anti-CD3+anti-CD28 activated Tr1 clones

FIG. 5: Phenotype of ovalbumin-specific Tr1 clones. (A) Surface CD25, GITR and intracellular Foxp3 and CTLA-4 expression were evaluated by flow cytometry on activated ovalbumin-specific Tr1 clones. (B) Kinetic of markers expression was evaluated after activation (Day0) and during 14 days in culture in the absence of stimuli.

FIG. 8: Analysis of remission in a patient. Analysis of CDAI (A), of abdominal pain (B) of liquid or soft stools per week (C) and of well being score (D).

DETAILED DESCRIPTION OF THE INVENTION

Definition

The term "Tr1 cells" as used herein refers to cells having the following phenotype at rest CD4+CD25-FoxP3- and capable of secreting high levels of IL-10 and low to moderate levels of TGF-β upon activation. Tr1 cells are characterized, in part, by their unique cytokine profile: they produce high levels of IL-10, significant levels of TGF-β and intermediate levels of IFN-γ, but little or no IL-4 or IL-2. The cytokine production is typically evaluated in cultures of cells after activation with polyclonal activators of T lymphocytes such as anti-CD3+ anti-CD28 antibodies or Interleukin-2, PMA+ ionomycin, Alternatively, the cytokine production is evaluated in cultures of cells after activation with the specific T-cell antigen presented by antigen presenting cells. High levels of IL-10 correspond to at least about 500 pg/ml, typically greater than about 1, 2, 4, 6, 8, 10, 12, 14, 16, 18, or 20 thousand pg/ml or more. Significant levels of TGF-β correspond to at least about 100 pg/ml, typically greater than about 200, 300, 400, 600, 800, or 1000 pg/ml or more. Intermediate levels of IFN-γ correspond to concentrations comprised between 0 pg/ml and at least 400 pg/ml, typically greater than about 600, 800, 1000, 1200, 1400, 1600, 1800, or 2000 pg/ml or more. Little or no IL-4 or IL-2 corresponds to less than about 500 pg/ml, preferably less than about 250, 100, 75, or 50 pg/ml, or less.

The term "antigen" as used herein refers to a protein, or peptide for which the cells of this invention are being used to modulate, or for use in any of the methods of this invention. In one embodiment, the term "antigen" may refer to a synthetically derived molecule, or a naturally derived molecule, which shares sequence homology with an antigen of interest, or structural homology with an antigen of interest, or a combination thereof. In one embodiment, the antigen may be a mimetope. A "fragment" of the antigen refers to any subset of the antigen, as a shorter peptide. A "variant" of the antigen refers to a molecule substantially similar to either the entire antigen or a fragment thereof. Variant antigens may be conveniently prepared by direct chemical synthesis of the variant peptide, using methods well-known in the art.

The term "subject" as used herein refers to a human being.

The term "effective amount" as used herein refers to an amount sufficient to cause a beneficial or desired clinical result (e.g. improvement in clinical condition).

The term "clone" or "clone population" as used herein refers to a population of differentiated cells being derived from a unique differentiated cell.

The term "treatment" or "treating" as used herein generally refers to a clinical intervention in an attempt to alter the natural course of the individual being treated, and may be performed during the course of clinical pathology. Desirable effects include, but are not limited to, alleviating symptoms, suppressing, diminishing or inhibiting any direct or indirect pathological consequences of the disease, lowering the rate of disease progression, ameliorating or palliating the disease state, and causing remission or improved prognosis.

THE PRESENT INVENTION

The present invention relates to a method for treating an intestinal inflammatory condition in a subject in need thereof, comprising the administration to said subject of a composition comprising human Tr1 cells directed against a food antigen from common human diet.

The term "food antigen from common human diet" refers to an immunogenic peptide, which comes from foodstuffs common for humans, such as food antigens of the following non-limiting list: bovine antigens such as lipocalin, Ca-binding SlOO, alpha-lactalbumin, lactoglobulins such as beta-lactoglobulin, bovine serum albumin, caseins. Food-antigens may also be atlantic salmon antigens such as parvalbumin, chicken antigens such as ovomucoid, ovalbumin, Ag22, conalbumin, lysozyme or chicken serum albumin, peanuts, shrimp antigens such as tropomyosin, wheat antigens such as agglutinin or gliadin, celery antigens such as celery profilin, carrot antigens such as carrot profilin, apple antigens such as thaumatin, apple lipid transfer protein, apple profilin, pear antigens such as pear profilin, isoflavone reductase, avocado antigens such as endochitinase, apricot antigens such as apricot lipid transfer protein, peach antigens such as peach lipid transfer protein or peach profilin, soybean antigens such as HPS, soybean profilin or (SAM22) PR-10 prot.

Without wishing to be bound to a theory, the Applicant assume that the injected Tr1 cell population directed to a food antigen from common human diet would be activated in vivo by the food antigen present in the intestinal tissue after common food intake and then would be able to control intestinal inflammatory conditions such as inflammatory bowel disease and inflammation linked to food allergy or intolerance.

The present invention relates to a composition comprising at least one human Tr1 cell population directed against a food antigen from common human diet.

In one embodiment of the invention, human Tr1 cells may be obtained by
a) isolating a progenitor cell population from a subject,
b) obtaining a population of dendritic cells by culturing said progenitor cell population in the presence of IL-10
c) contacting cells of step b) with a CD4+ T lymphocyte population isolated from said subject in the presence of a food antigen to allow differentiation of CD4+ T cells directed to said antigen into the Tr1 cell population, and
d) recovering the Tr1 cell population from the step c).

In step b), IL-10 is present from 50 to 250 U/ml, preferably at 100 U/ml in the culture medium. Said method for obtaining Tr1 cells is described in Wakkach et al (Immunity 2003 May; 18(5):605-17).

Said method may also be carried out using Dexamethasone and Vitamin D3, or tolerogenised or immature DCs instead of the DCs of step b).

In another embodiment of the present invention, human Tr1 cells may be obtained by:
a) culturing a CD4+ T cell population directed to a food antigen isolated from a subject in a media with an appropriate amount of IFN-α, and
b) recovering the Tr1 cell population.

IFN-α is preferably present in the media at 5 ng/ml. In the step a), the media may further comprise an appropriate amount of IL-10, preferably at 100 U/ml.

In step b), the Tr1 cell population is cultured in a media comprising IL-15 to allow proliferation, IL-15 being preferably at 5 ng/ml in the media. Said method for obtaining Tr1 cells is described in the U.S. Pat. No. 6,746,670.

In still another embodiment of the invention, human Tr1 cells may be obtained by:
a) in vitro activating a CD4+ T cell population in presence of a food antigen, presented by artificial antigen presenting cells, and
b) recovering an activated CD4+ T cells comprising at least 10% of Tr1 cells.

Preferably, the artificial antigen presenting cells express a HLA II system molecule and a human LFA-3 molecule and don't express the co-stimulation molecules B7-1, B7-2, B7-H1, CD40, CD23 and ICAM-1.

Said process, for obtaining Tr1 cells is described in the patent application WO02/092793.

In still another embodiment of the invention, human Tr1 cells may be obtained by:
a) in vitro activating a CD4+ T cell population in presence of a food antigen and an appropriate amount of IL-10; and
b) recovering the Tr1 cell population.

Preferably, IL-10 is present in the media at 100 U/ml. Said method is described in Groux et al. (Nature 1997, 389(6652): 737-42).

In still another embodiment of the invention, human Tr1 cells may be obtained by:
a) stimulating a leukocyte population or a peripheral blood mononuclear cell (PBMC) population with a food antigen,
b) recovering the antigen-specific Tr1 cell population from the stimulated population,
c) optionally expanding said antigen-specific Tr1 cell population.

Leukocytes encompass several types of cells, which are characterized by their importance, their distribution, their number, their lifetime and their potentiality. These types are the following: the polynuclear or granular leukocytes, among which one finds the eosinophilic, the neutrophilic and the basophilic leukocytes, and the mononuclear cells, or peripheral blood mononuclear cells (PBMCs), which are large white blood cells and consist in the cell types of the immune system (lymphocytes and monocytes). The leukocytes or the PBMCs can be separated from the peripheral blood by any method known to those skilled in the art. Advantageously, for the separation of the PBMCs, centrifugation may be used, preferably density gradient centrifugation, preferably discontinuous density gradient centrifugation. An alternative is the use of specific monoclonal antibodies. In certain embodiments PBMC are typically isolated from the whole blood product by means of Ficoll-Hypaque, using standard procedures. In other embodiments the PBMCs are recovered by means of leukopheresis.

Said method is described in the patent application WO2007/010406.

In still another embodiment, human Tr1 cells may be obtained by:
a) culturing a leukocyte population or a peripheral blood mononuclear cell (PBMC) population with mesenchymal stem cells in the presence of a food antigen,
b) recovering the Tr1 cell population.

Said method can also be carried out with naïve or memory T cells instead of PBMC or leukocytes.

The Tr1 cell population thus obtained may further be expanded by culture in presence of cytokines such as Interleukine-2 and Interleukine-4. Alternatively, Interleukine-15 and Interleukine-13 could also be used in Tr1 cell expansion cultures.

In the methods described above, human Tr1 cells can be characterized by the identification method described in WO2005/000344. Said identification method of Tr1 cells is based on the detection of the simultaneous presence of expression products of genes coding CD4 molecule and molecules from the group comprising CD18 and/or CD11a, and CD49b. Tr1 cells can be identified and/or purified by Elisa, flow cytometry, or immunoaffinity methods with antibodies directed against said markers.

Tr1 cells can also be enriched by positive selection or negative selection using flow cytometry or magnetic beads. Such methods are also described in WO2005/000344.

In another embodiment of the present invention, the Tr1 cells directed to a food antigen from human common diet antigen may be expanded by the in vitro method described in WO2006/108882. Said method comprises:
a) cultivating at a temperature T1 inferior to 35° C., in a culture medium Mf, feeder cells such as insect feeder cells, said temperature T1 allowing the proliferation of feeder cells and said feeder cells expressing factors which interact with the following cell surface proteins:
the CD3/TCR complex,
the CD28 protein,
the IL-2 receptor, the CD2 protein,
the IL-4 receptor, b) contacting the feeder cells obtained in step a) cleared or not of their culture medium Mf, with the Tr1 cell population contained in the culture medium Mp, wherein said culture medium Mp does not initially contain the factors cited in step a), in order to obtain a mixture containing the Tr1 cell population, the feeder cells and the culture medium Mp, c) cultivating the mixture obtained at step b) at a temperature T2 which is at least 35° C., said temperature being chosen such that the Tr1 cell population proliferates and the feeder cells do not proliferate, d) recovering the Tr1 cell population such expanded.

Examples of factors which interact with the above mentioned cell surface proteins include:
a modified anti-CD3 antibody, wherein the anti-CD3 intracytoplasmic domain of the CD3 heavy chain is replaced with a transmembrane domain,
the CD80 or CD86 protein,
the IL-2 secreted by the feeder cells,
the CD58 protein,
an interleukin selected from the group comprising IL-4 and IL-13.

In a preferred embodiment of the present invention, said Tr1 cells directed to food antigen from common human diet may be cloned by using conventional methods for cloning T cells.

In preferred embodiment of the present invention, said composition comprising at least one human Tr1 cell population directed against a food antigen from common human diet or at least one clone of human Tr1 cell directed against a food antigen from common human diet may be frozen to be stored.

In a preferred embodiment of the present invention, said food antigen from common human diet is selected from the group comprising bovine antigens, Ca-binding SlOO, alpha-lactalbumin, lactoglobulins such as beta-lactoglobulin, bovine serum albumin, caseins, atlantic salmon antigens, chicken antigens, ovalbumin, Ag22, conalbumin, lysozyme or chicken serum albumin, shrimp antigens, wheat antigens such as gluten proteins: gliadin, celery antigens, carrot antigens, apple antigens, apple lipid transfer protein, apple profilin, pear antigens, isoflavone reductase, avocado antigens, apricot antigens, peach antigens, soybean antigens, peanuts, fragments, variants and mixtures thereof. Preferably, the food antigen is a recombinant or a synthesized antigen.

Preferably, said food antigen from common human diet is ovalbumin, casein, beta-lactoglobulin, soya protein, gliadin, peanuts, fragments, variants and mixtures thereof.

More preferably, said food antigen from common human diet is ovalbumin, fragments and variants thereof.

More preferably, said food antigen from common human diet is gliadin, fragments and variants thereof.

More preferably, said food antigen from common human diet is casein, fragments and variants thereof.

More preferably, said food antigen from common human diet is beta-lactoglobulin, fragments and variants thereof.

More preferably, said food antigen from common human diet is peanut, fragments and variants thereof.

The term "variant" of the food antigen from common human diet refers herein to an antigen that is almost identical to the natural antigen and which shares the same biological activity. The minimal difference between the natural antigen and its variant may lie for example in an amino-acid substitution, deletion, and/or addition. Such variants may contain for example conservative amino acid substitutions in which amino acid residues are replaced with amino acid residues having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta.-branched side chains (e.g., threonine, valine, isoleucine) and aromatic side chains (e.g., tyrosine, phenylalanine, tryptophan, histidine).

Another object of the present invention is to provide a medicament comprising a composition as described here above.

The present invention also intends to provide a pharmaceutical composition comprising a composition as described here above in combination with one or more pharmaceutically acceptable carrier.

The pharmaceutically acceptable carriers useful herein are conventional. Remington's Pharmaceutical Sciences 16$^{th}$ edition, Osol, A. Ed. (1980) describes composition and formulations suitable for pharmaceutical delivery of the composition of the present invention. In general, the nature of the carrier will depend on the mode of administration being employed. For instance, parenteral formulations usually comprise injectable fluids that include pharmaceutically and physiologically acceptable fluids such as water, physiological saline, balanced salt solutions, aqueous dextrose, sesame oil, glycerol, ethanol, combinations thereof, or the like, as vehicle. The carrier and composition can be sterile, and the formulation suits the mode of administration. In addition to biological neutral carriers, pharmaceutical compositions to be administrated can contain minor amounts of non toxic auxiliary substances, such as wetting or emulsifying agents, preservatives, and pH buffering agents and the like, for example sodium acetate or sorbitan monolaurate. The composition can be a liquid solution, suspension, emulsion.

In one embodiment of the invention, said medicament or pharmaceutical composition as described here above consists essentially of at least one Tr1 cell population directed against a food antigen from common human diet.

In another embodiment of the invention, said medicament or pharmaceutical composition as described here above consists essentially of at least one clone of a Tr1 cell population directed against a food antigen from common human diet.

As used herein, "consists essentially of" refers to a medicament or a pharmaceutical composition, wherein at least 70%, preferably 75%, 80%, 85% or 90% of the cells present in the medicament or pharmaceutical composition are Tr1 cells directed against a food antigen from common human diet.

In one embodiment of the invention, said medicament or pharmaceutical composition as described here above comprises Tr1 cell population directed against a food antigen from common human diet, excepted gliadin.

In another embodiment of the invention, said medicament or pharmaceutical composition as described here above consists of at least one Tr1 cell population directed against a food antigen from common human diet or at least one clone of a Tr1 cell population directed against a food antigen from common human diet.

In another embodiment of the invention, said medicament or pharmaceutical composition as described here above consists of at least one Tr1 cell population directed against a food antigen from common human diet or at least one clone of a Tr1 cell population directed against a food antigen from common human diet, excepted gliadin.

The present invention relates to the use of a composition as described here above for the preparation of a medicament or a pharmaceutical composition for treating an intestinal inflammatory condition.

According to the invention, the pharmaceutical composition or medicament as described here above is for treating an intestinal inflammatory condition.

According to the invention, the pharmaceutical composition or medicament as described here above is for use in the treatment of an intestinal inflammatory condition.

According to the invention, said pharmaceutical composition or medicament is not used in combination with the soluble food antigen from common human diet.

According to the invention, said pharmaceutical composition or medicament is not administrated to the subject together with or in combination with the soluble food antigen from common human diet.

According to the invention, there is no need for a co-treatment with the soluble food antigen from common human diet to which the Tr1 cells are directed.

In one embodiment, the present invention relates to the use of a composition as described here above for the preparation of a medicament or a pharmaceutical composition for treating inflammatory bowel disease.

In a preferred embodiment, the present invention relates to the use of a composition as described here above for the preparation of a medicament or a pharmaceutical composition for treating Crohn's disease.

In another preferred embodiment, the present invention relates to the use of a composition as described here above for the preparation of a medicament or a pharmaceutical composition for treating ulcerative colitis.

In another embodiment, the present invention relates to the use of a composition as described here above for the preparation of a medicament or a pharmaceutical composition for treating intestinal inflammation linked to food allergy or intolerance.

In a preferred embodiment, the present invention relates to the use of a composition as described here above for the preparation of a medicament or a pharmaceutical composition for treating intestinal inflammation linked to milk protein allergy. Preferably, said medicament or a pharmaceutical composition for treating intestinal inflammation linked to milk protein allergy comprises human Tr1 cells directed to casein or beta-lactoglobulin, fragments and variants thereof.

In another preferred embodiment, the present invention relates to the use of a composition as described here above for the preparation of a medicament or a pharmaceutical composition for treating intestinal inflammation linked to celiac disease. Preferably, said medicament or a pharmaceutical composition for treating intestinal inflammation linked to celiac disease comprises human Tr1 cells directed to gliadin, fragments and variants thereof.

In another preferred embodiment, the present invention relates to the use of a composition as described here above for the preparation of a medicament or a pharmaceutical composition for treating intestinal inflammation linked to hen egg allergy. Preferably, said medicament or a pharmaceutical composition for treating intestinal inflammation linked to hen egg allergy comprises human Tr1 cells directed to ovalbumin, fragments and variants thereof.

In another preferred embodiment, the present invention relates to the use of a composition as described here above for the preparation of a medicament or a pharmaceutical composition for treating intestinal inflammation linked to peanut allergy. Preferably, said medicament or a pharmaceutical composition for treating intestinal inflammation linked to peanut allergy comprises human Tr1 cells directed to peanut, fragments and variants thereof.

An object of the present invention is also a method for treating inflammatory bowel diseases, preferably Crohn's disease or ulcerative colitis, in a subject in need thereof, comprising administering to said subject an effective amount of a medicament as described here above or a pharmaceutical composition as described here above.

Another object of the present invention is a method for treating intestinal inflammation linked to food allergy or intolerance, preferably milk protein allergy, celiac disease, hen egg allergy or peanut allergy, in a subject in need thereof, comprising administering to said subject an effective amount of a medicament as described here above or a pharmaceutical composition as described here above.

The composition may be formulated for parenteral, intramuscular, intravenous, intraperitoneal, injection, intranasal inhalation, lung inhalation, intradermal, intra-articular, intrathecal, or via the alimentary tract. In another embodiment, the composition may be formulated for intra-tissular or intra-mucosal administration via endoscopic route, to deliver the composition directly in colon or in the small intestine.

Preferably, the medicament or pharmaceutical composition of the invention may be administrated by intramuscular, intraperitoneal or intravenous injection, or by direct injection into the lymph nodes of the patient, preferably by intravenous injection.

The amount of Tr1 cells directed to a food antigen from common human diet effective in the treatment of an intestinal inflammatory condition such as inflammatory bowel disease and intestinal inflammation linked to food allergy or intolerance will depend on the nature of the inflammation, and can be determined by standard clinical techniques. The precise dose to be employed in the formulation will also depend on the route of administration, and the seriousness of the disease or disorder, and should be decided according to the judgment of the practitioner and each individual's circumstances. Effective doses can be extrapolated from dose-response curves derived from in vitro or animal model test systems.

In one embodiment of the present invention, $10^4$/kg to $10^9$/kg cells are administrated to the subject. Preferably $10^5$/kg to $10^7$/kg cells and more preferably about $10^6$/kg cells are administrated to the subject.

In one embodiment of the invention, the subject is administrated with the medicament at the time when flare-up are demonstrated by a decline in the clinical status of the subject or at the time when inflammatory lesions can be visualized for example by endoscopic examinations.

In one embodiment of the invention, the subject is administrated once with the medicament or the pharmaceutical composition of the present invention.

In a second embodiment of the invention, the subject is administrated once a month with the medicament or the pharmaceutical composition of the present invention.

In a third embodiment of the invention, the subject is administrated once a quarter with the medicament or the pharmaceutical composition of the present invention.

In a fourth embodiment of the invention, the subject is administrated once to twice a year with the medicament or the pharmaceutical composition of the present invention.

In another embodiment of the present invention, the medicament or pharmaceutical composition to be administered to a subject in need thereof comprises human Tr1 cells autologous to the cells of said subject.

This means that Tr1 cells will be administrated to the subject they come from or that precursors used for the production of Tr1 cells come from the subject the Tr1 cells will be administrated to.

The present invention relates also to a process for treating an intestinal inflammatory condition in a subject in need thereof, said process comprising the steps of:
  collecting a blood sample of said subject,
  obtaining Tr1 cells directed to a selected food antigen from common human diet,
  cloning said Tr1 cells directed to a selected a food antigen from common human diet,
  further expanding Tr1 clones obtained at the previous step,
  re-injecting Tr1 clones thus obtained in said subject, preferably by intravenous route.

Preferably, cloning and expansion of Tr1 clones directed to a selected food antigen from common human diet is carried out with the following method:
a) cultivating at a temperature T1 inferior to 35° C., in a culture medium Mf, feeder cells such as insect feeder cells, said temperature T1 allowing the proliferation of feeder cells and said feeder cells expressing factors which interact with the following cell surface proteins:
  the CD3/TCR complex,
  the CD28 protein,
  the IL-2 receptor,
  the CD2 protein,
  the IL-4 receptor,
b) contacting the feeder cells obtained in step a) cleared or not of their culture medium Mf, with the Tr1 cell population contained in the culture medium Mp, wherein said culture medium Mp does not initially contain the factors cited in step a), in order to obtain a mixture containing the Tr1 cell population, the feeder cells and the culture medium Mp,
c) cultivating the mixture obtained at step b) at a temperature T2 which is at least 35° C., said temperature being chosen such that the Tr1 cell population proliferates and the feeder cells do not proliferate,
d) recovering the Tr1 cell population such expanded.

Examples of factors which interact with the above mentioned cell surface proteins include
  a modified anti-CD3 antibody, wherein the anti-CD3 intracytoplasmic domain of the CD3 heavy chain is replaced with a transmembrane domain,
  the CD80 or CD86 protein,
  the IL-2 secreted by the feeder cells,
  the CD58 protein,
  an interleukin selected from the group comprising IL-4 and IL-13.

In another embodiment of the present invention, the method for treating an intestinal inflammatory condition, such as inflammatory bowel diseases or intestinal inflammation linked to food allergy or intolerance, in a subject in need thereof comprises the administration to said subject of an effective amount of the medicament or the pharmaceutical composition of the invention in combination with one or more therapeutic agent used for treating an intestinal inflammatory condition.

The present invention relates to the use of the pharmaceutical composition or medicament of the invention, wherein the administration to said subject of an effective amount of the medicament or the pharmaceutical composition of the invention is in combination with one or more therapeutic agent used for treating an intestinal inflammatory condition.

Examples of therapeutic agents commonly used for treating an intestinal inflammatory condition are the following:
  antibodies or antagonists of human cytokines or growth factors, in particular, anti-TNF such as infliximab, adalimumab, etanercept; anti-IL1, anti-IL-6, anti-IL-12, anti-IL-17 and anti-IL-23; IL-1 receptor antagonist analogs (anakinra)
  antibodies to cell surface molecules such as anti-α4 integrin (natalizumab), CD2, CD3 (visiluzumab), anti-CCR9, anti-LFA1 and anti-ICAM1;
  5 aminosalicyclic acid and analogs such as mesalazine, sulfazaline, olsalazine, balsalazide;
  corticoids such as prednisone, budesonide, hydrocortisone, prednisolone, methylprednisolone, betamethasone, bedomethasone, tixocortol;
  probiotics such as *saccharomyces* boulardii;
  methotrexate, thalidomide, leflunomide, and analogs of purines such as Azathioprine and 6-mercaptopurine.

In a preferred embodiment of the present invention, the method for treating an intestinal inflammatory condition in a subject in need thereof comprises the administration to said subject of an effective amount of the medicament or the pharmaceutical composition of the invention in combination with one or more therapeutic agent selected in the group of anti-TNF, natalizumab, anti-IL1, anti-IL-6, anti-IL-12, anti-IL-17 and anti-IL-23; IL-1 receptor antagonist analogs (anakinra); 5 aminosalicyclic acid and analogs such as mesalazine, sulfazaline, olsalazine, balsalazide; corticoids such as prednisone, budesonide, hydrocortisone, prednisolone, methylprednisolone, betamethasone, bedomethasone, tixocortol.

The present invention relates to the use of the pharmaceutical composition or medicament of the invention for treating an intestinal inflammatory condition in a subject in need thereof, wherein the administration to said subject of an effective amount of the medicament or the pharmaceutical composition of the invention is in combination with one or more therapeutic agent selected in the group of anti-TNF, natalizumab, anti-ILL anti-IL-6, anti-IL-12, anti-IL-17 and anti-IL-23; IL-1 receptor antagonist analogs (anakinra); 5 aminosalicyclic acid and analogs such as mesalazine, sulfazaline, olsalazine, balsalazide; corticoids such as prednisone, budesonide, hydrocortisone, prednisolone, methylprednisolone, betamethasone, bedomethasone, tixocortol.

In another embodiment, the present invention also relates to a method of treatment of an intestinal inflammatory condition in which the medicament or the pharmaceutical composition of the invention is to be administrated to a subject in need thereof, wherein the subject does not respond adequately to, or is unlikely to respond adequately to, one or more therapeutic agent in the group of anti-TNF, natalizumab, anti-ILL anti-IL-6, anti-IL-12, anti-IL-17 and anti-IL-23; IL-1 receptor antagonist analogs (anakinra); 5 aminosalicyclic acid and analogs such as mesalazine, sulfazaline, olsalazine, balsalazide; corticoids such as prednisone, budesonide, hydrocortisone, prednisolone, methylprednisolone, betamethasone, bedomethasone, tixocortol, probiotics such as *saccharomyces* boulardii, methotrexate, azathioprine, 6-mercaptopurine, thalidomide, leflunomide.

The present invention relates to the use of the pharmaceutical composition or medicament of the invention, wherein said subject does not respond adequately to, or is unlikely to respond adequately to, one or more therapeutic agent in the group of anti-TNF, natalizumab, anti-ILL anti-IL-6, anti-IL-12, anti-IL-17 and anti-IL-23; IL-1 receptor antagonist analogs (anakinra); 5 aminosalicyclic acid and analogs such as mesalazine, sulfazaline, olsalazine, balsalazide; corticoids such as prednisone, budesonide, hydrocortisone, prednisolone, methylprednisolone, betamethasone, bedomethasone, tixocortol, probiotics such as *saccharomyces* boulardii, methotrexate, azathioprine, 6-mercaptopurine, thalidomide, leflunomide.

"Inadequate response", "does not respond adequately to", or "unlikely to respond adequately" refer to an actual or probable response by a subject which indicates that the therapy has been, or is likely to be, ineffective, toxic, or poorly tolerated insofar as the subject is concerned.

EXAMPLES

In the following description, all experiments for which no detailed protocol is given are performed according to standard protocol.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Experiment 1

Experimental Procedures

Mice 7-weeks old female Balb/c mice were obtained from Janvier (Le Genest-St-Isle, France).

TR1 Cell Differentiation

Balb/c splenocytes were first cultured at $2.510^6$ cells/ml in Yssel medium supplemented with IL-2 (100 UI/ml) plus IL-4 (20 ng/ml) in the presence of the Soy or Fish proteins found in common breeding mouse diet (SAFE). Cells were cultured at 37° C., 5% CO2 and divided when required in the same culture medium. Mouse T cells were then stimulated once a week in the presence of $4.10^5$ irradiated autologous splenocytes in 24-well plates and in presence of the Soy or Fish proteins. T-cell populations were restimulated once a week during two or five weeks.

Cytokine Assays

Sandwich ELISAs were performed on 48 hours supernatants of T-cell populations ($5.10^5$ cells) stimulated with the specific antigen (fish or soy proteins) in the presence or absence of irradiated autologous splenocytes ($4.10^5$). ELISAs were performed using anti-IL-4 (11B11), anti-IL-10 (2A5), anti-IFN-γ (XGM1.2), biotin anti-IL-4 (24G2), anti-IL-10 (SXC1), anti-IFN-γ (R4-6A2) (Pharmingen Becton Dickinson).

Colitis Induction

For colitis induction, Dextran sodium sulfate (DSS, ICN, Biomedicals) was added in the drinking water of mice from day 0 to day 5.

Results

Use of Mouse TR1 Directed to Food Antigen for Treating Colitis in Mice

In these experiments, mouse Tr1 cells directed against fish proteins and soy proteins were used, as proteins from fish flour and soy proteins are common food antigen for breeding mice.

Figure 1:
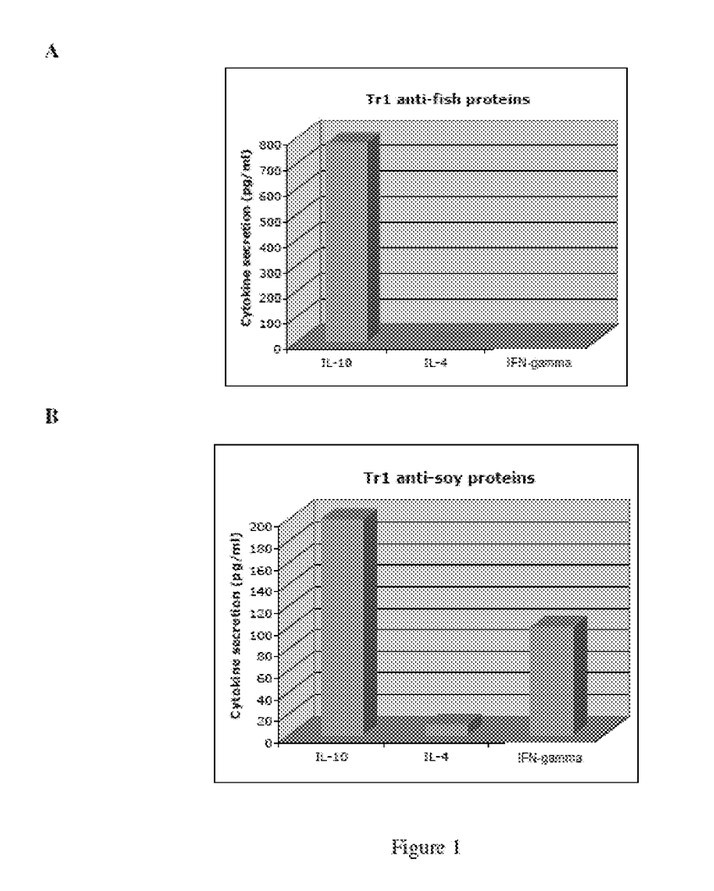
FIG. 1: Cytokines expression profile of mouse anti-fish proteins Tr1 and mouse anti-soy proteins Tr1 lymphocytes.

FIG. 1 shows the cytokine expression profile of Tr1 cells specific for fish proteins (FIG. 1A) and soy proteins (FIG. 1B).

Mice were treated with 5% DSS in water during 5 days to induce acute inflammatory colitis and weight of the mice was measured in day 5, 6 and 7.

Figure 2:
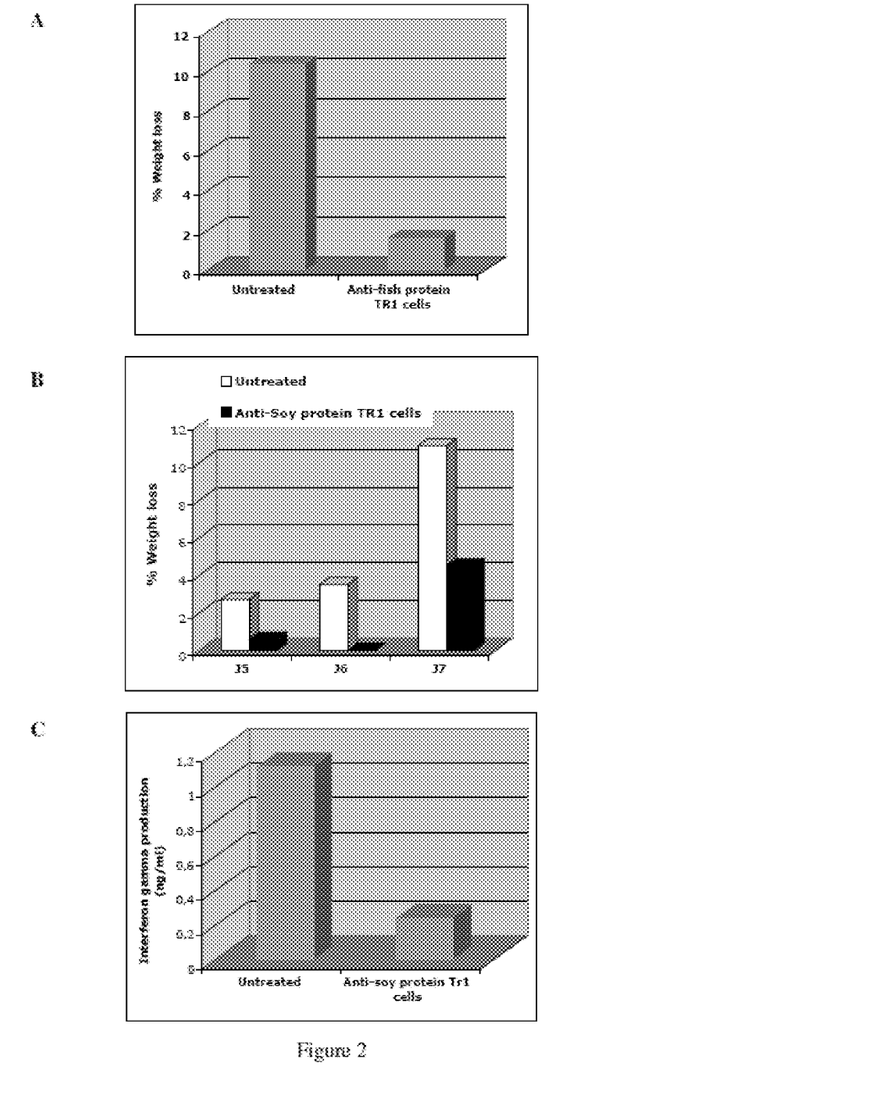
FIG. 2: Mouse anti-fish proteins and mouse anti-soy proteins Tr1 cells control inflammatory colitis in mice. (A and B) Analysis of weight loss. (C) Production of IFN-γ by mouse anti-soy proteins Tr1 cells.

In FIG. 2A, first group of mice was untreated and second group was injected on day 1 with $10^6$ mouse anti-fish Tr1 cells.

In FIG. 2B, first group of mice was untreated and second group was treated on day 1 and 3 with $4.10^5$ mouse anti-soy Tr1 cells and on day 6 with $3.10^5$ mouse anti-soy Tr1 cells.

FIG. 2C shows that IFN-γ production at day 8 by colon cells is also inhibited by administration of mouse anti-soy Tr1 cells.

Results of these experiments show that administration of Tr1 cells directed to a food antigen from common mouse diet results in an inhibition of weight loss and allows control of inflammatory colitis induced by DSS in mice.

Experiment 2

Experimental Procedures

Ovalbumin Specific Tr1 Clone Production

Ovalbumin specific Tr1 clones were produced from Peripheral Blood Mononuclear Cells (PBMC) of healthy donors or Crohn's Disease patients. After PBMC isolation by Ficoll gradient density centrifugation (GE Healthcare, Uppsala, Sweden), cells were cultured in the presence of native irradiated ovalbumin (Sigma Aldrich, St-Louis, Mo., USA) in X-Vivo15 (Cambrex, East Rutherford, N.J.) and cytokine-enriched *Drosophila* feeder cell supernatants at 37° C., 5% $CO_2$. After several days of culture, cells are cloned by limiting dilution method on layers of *Drosophila* feeder cells in X-Vivo15 at 37° C., 5% $CO_2$. Growing clones are then harvested and tested for antigen specificity and Tr1 cell identity before being expanded on *Drosophila* feeder cells up to 5 billions.

*Drosophila* Feeder Cells

*Drosophila* feeder cells were engineered by TxCell in order to improve the stimulation and growth of Tr1 cell clones. Schneider *Drosophila* cells were transfected with a transmembrane form of a murine anti-human CD3 antibody, with human CD80, human CD58, human IL-2 and human IL-4. Cells are grown routinely in Express five medium from PAA laboratories (Pashing, Austria).

Cytokine Assays

For the determination of antigen specificity, sandwich ELISAs were performed on 48 hours supernatants of T-cell clones stimulated in the presence of antigen presenting cells ($4.10^5$) and in the presence or absence of the specific antigen (ovalbumin). For the determination of the cytokine production profile, ovalbumin specific Tr1 cell clones were stimulated with anti-CD3+anti-CD28 monoclonal antibodies coated beads (Invitrogen, Carlsbad, Calif.) and the supernatants were harvested after 48 hours. ELISAs were performed using commercially available kits from Diaclone (Besancon, France).

Suppression Assays

For suppression studies in co-culture, graded quantities of ovalbumin specific Tr1 clones were co-cultured with autologous CD4+ T lymphocytes. Co-cultures were stimulated with anti-CD3+anti-CD28 monoclonal antibodies coated beads. After 3 days, total cell proliferation was assessed using the WST-1 proliferation kit from Roche (Roche Applied. Science, Basel, Switzerland). Suppression of autologous CD4+

T-cell proliferation was also evaluated using diluted supernatants of Tr1 cell activated with anti-CD3+anti-CD28 monoclonal antibodies coated beads during 48 hours. Anti-IL-10 and anti-TGFbeta monoclonal antibodies were purchased from R&D systems and were used at 10 µg/ml.

Toxicology Studies

Karyotypes of Tr1 clones were performed at the "laboratoire Genazur" (Nice, France). Telomeres length measurements were performed according to a standard procedures (13) by the team of G. Butler brown (Institute of myology, Inserm U787, Paris). Clonogenicity evaluations were performed by seeding Tr1 cells at 1 cell/well in 96 well-plates in X-Vivo15 with or without growth factors (IL-2, 200 UI/ml and IL-4, 20 ng/ml; purchased from R&D systems, Minneapolis, Minn.) or at 40 000 cells/ml in semi-solid agar based medium with or without growth factors. Evaluation of clone's growth was performed once a week for 8 consecutive weeks.

Results

Figure 3:
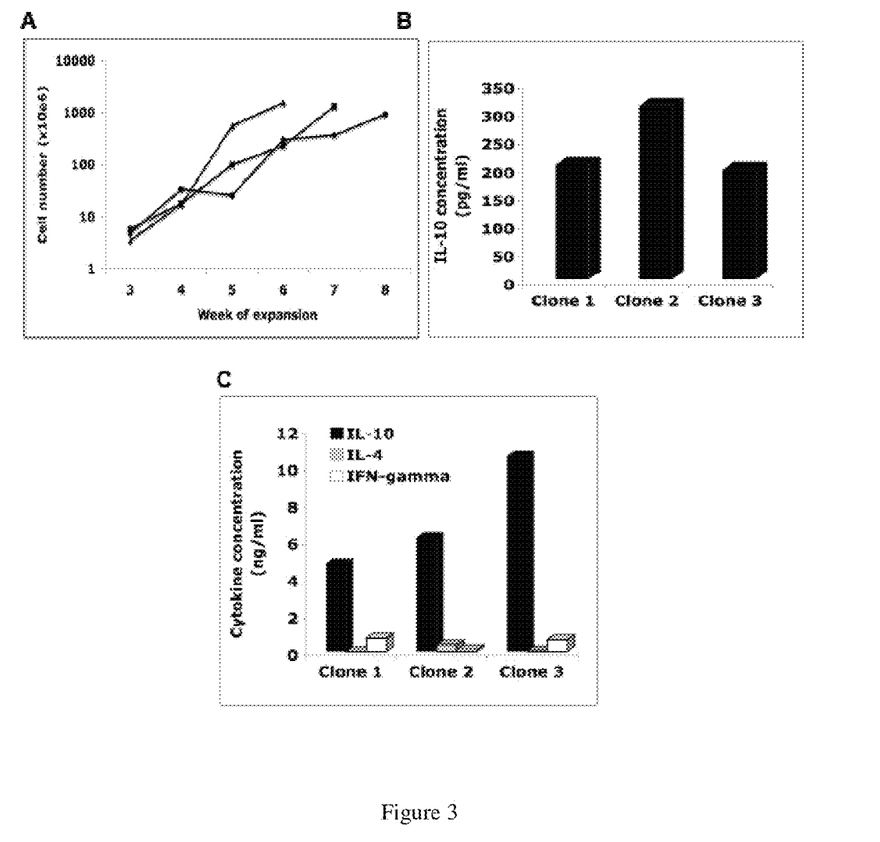

The manufacturing process for anti-ovalbumin specific Tr1 cells was first developed with peripheral blood cells from healthy donors. The first step involves a culture of peripheral blood mononuclear cells with native ovalbumin, IL-2 and IL-4 in order to enrich/expand ovalbumin specific T lymphocytes. At the end of this step, cells are cloned by limiting dilution method. Cloning of the T cells and further expansion of the T-cell clones are achieved by seeding the ovalbumin-specific T cell enriched PBMCs on a layer of feeder cells from drosophila origin (Schneider cells) stably transfected with a transmembrane form of an anti-CD3 monoclonal antibody, human CD80, human CD58, human IL-2 and human IL-4. This strategy, leads to an efficient proliferation of the T-cell clones (FIG. 3a). This method allows the production of more than 5 billions of a monoclonal Tr1 cell population in 12 to 15 weeks. During the expansion step, growing clones are evaluated for their specificity to ovalbumin and for their Tr1 specific identity. Specificity to ovalbumin is observed by the production of IL-10 detected by ELISA in the supernatant of cell clones cultured in presence of ovalbumin presented by irradiated autologous PBMCs. Tr1 cell identity is also observed by ELISA after polyclonal activation of the clones with anti-CD3+ anti-CD28 coated beads. Examples of selected clones are presented in the FIG. 3 panel B and C. Importantly, in this process, the use of drosophila feeder cells allows the expansion of Tr1 cells in the complete absence of animal or human serum. Results of this process development on more than 50 healthy donors shows that ovalbumin specific Tr1 cells could be isolated in a vast majority of the individuals with this method (more than 90%). This suggests that tolerance to ovalbumin and more largely to diet antigens is in part achieved by a suppressive mechanism involving Tr1 cells implicating thus this population of suppressive cells as central regulatory effectors of oral tolerance.

Figure 4:
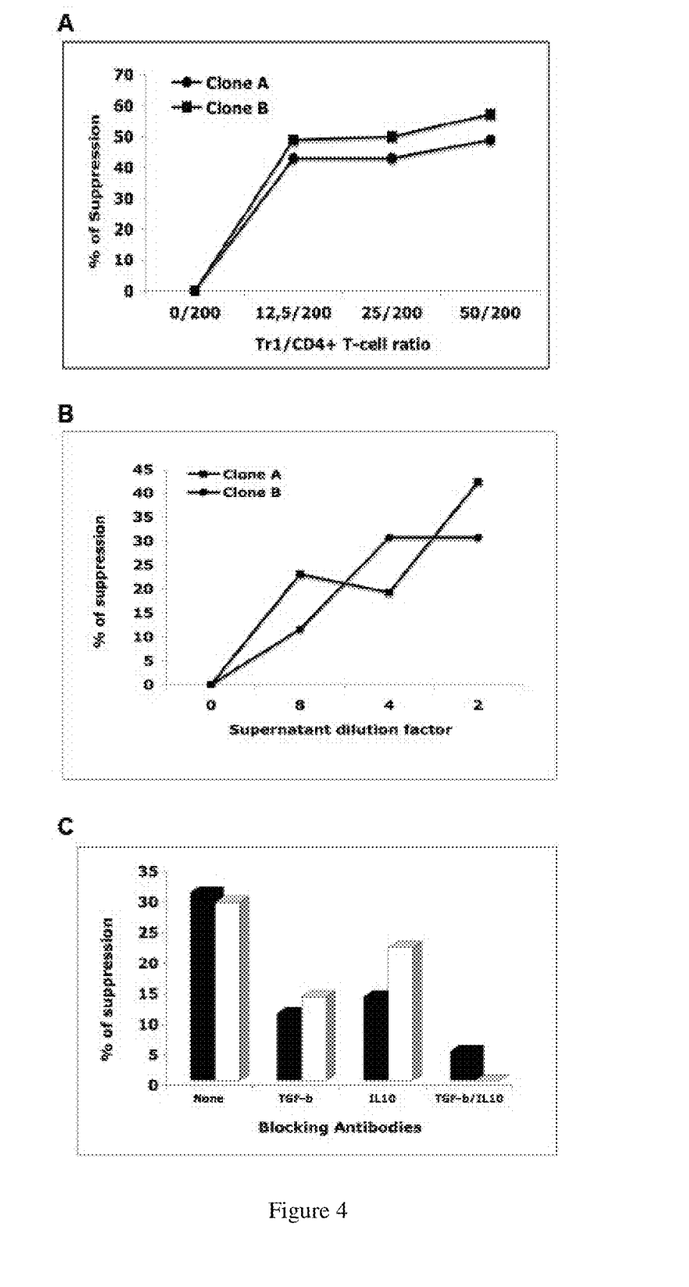
FIG. 4: Ovalbumin specific-Tr1 clone suppressive activity. Example of 2 different clones. (A) Suppressive activity of graded concentration of ovalbumin-specific Tr1 clones on the proliferation of autologous CD4+ T cells in co-culture. (B) Suppressive activity of diluted culture supernatants of activated ovalbumin Tr1 clones on autologous CD4+ T cells. (C) Blockade of Tr1 supernatant mediated T-cell proliferation by IL-10 and TGF-beta monoclonal antibodies.
Figure 5:
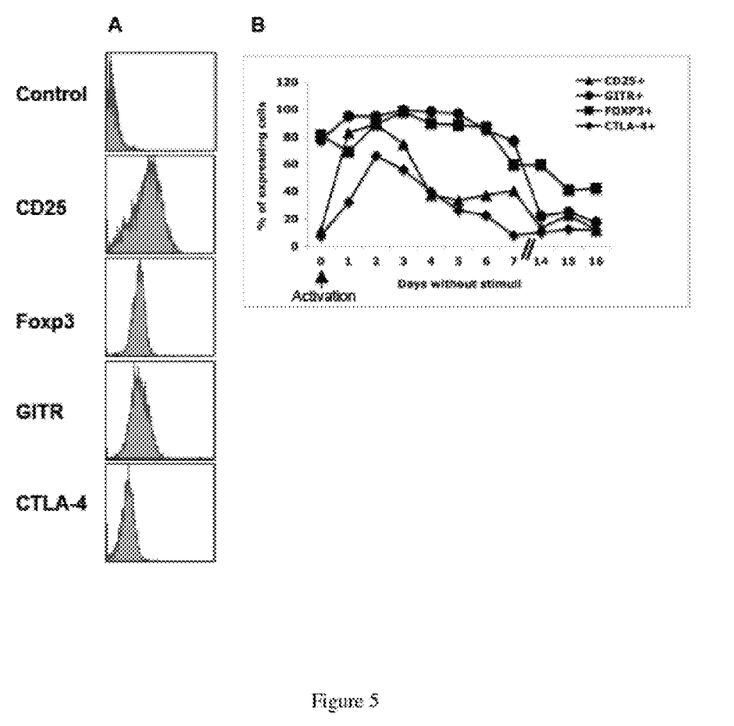

In order to characterize in more depth the selected Tr1 cell clones, we analyzed their suppressive function in vitro in conventional suppression assay. For this purpose, purified CD4+ T lymphocytes were activated in vitro with anti-CD3 and anti-CD28 monoclonal antibodies coated beads in the presence of graded quantities of Tr1 clones selected from the same donor. FIG. 4 shows that in these experiments, Tr1 cells even at a ration of 1 per 16 target cells inhibit the proliferation of autologous CD4+ T lymphocytes (FIG. 4, Panel A). In the same kind of proliferation assay, culture supernatant of Tr1 clones activated in vitro with anti-CD3 and anti-CD28 monoclonal antibodies coated beads also displays a suppressive activity that although more discrete than the contact-mediated suppression is consistently observed (FIG. 4, Panel B) suggesting that the inhibitory action of Tr1 cells on T-cell proliferation is in part mediated by soluble factors. Not surprisingly, the suppressive action of these supernatants was inhibited by blocking antibodies to IL-10 and TGF-beta (FIG. 4, Panel C). These different experiments show that the cells isolated following our procedures display a suppressive capacity reminiscent to that described for Tr1 cells. Indeed, IL-10 and TGF-beta produced by activated Tr1 clones act to inhibit T-cell proliferation and blockade of both cytokines completely blocks the suppressive action of Tr1 cell supernatants showing that these soluble factors act in synergy to dampen T-cell proliferation. To further confirm the Tr1 identity of the selected clones on a phenotypic basis, we evaluated their surface expression of regulatory cell markers CD25, Foxp3, GITR and CTLA-4. All these molecules are expressed by the majority of activated Tr1 cells and are downregulated at the resting state after leaving the cells in culture without stimuli during several days (FIG. 5).

Figure 6:
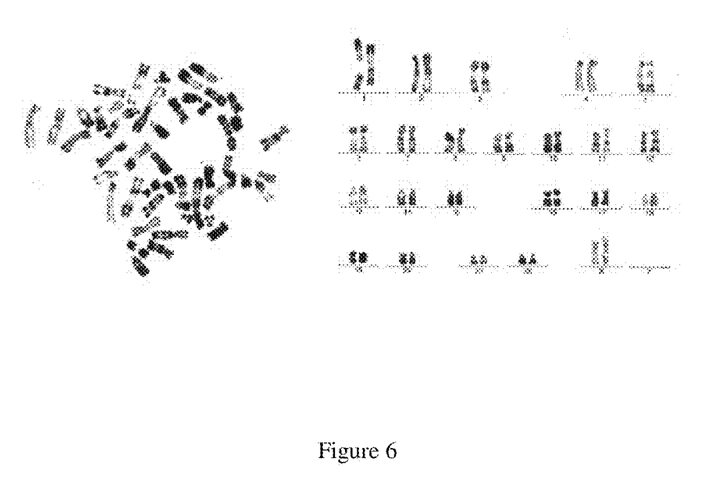
FIG. 6: Karyotypic examination of an ovalbumin-specific Tr1 clone expanded in vitro with *Drosophila* derived feeder cells and having performed more than 30 doublings

Since this manufacturing process development aims at producing cells for injection to patients, experiments were performed to show the absence of genetic aberrations or deregulation of cell survival/proliferative characteristics in the produced T-cell clones. Karyotypes were performed on 4 clones from different donors and always show normal profiles (FIG. 6). We also analyzed the survival capacity of Tr1 clones under chronic stimulation with Drosophila feeder cells by the evaluation of the maximum of doublings performed before senescence and by the evaluation of the clonogenicity potential of the clones in liquid and semi-solid medium (Table 1). Finally, doubling times and telomere length were compared between clones having doubled 30 times (equivalent of $10^9$ cells) and cells having doubled 10 more times (Table 1). All these experiments showed a normal regulation of proliferation and senescence in the Tr1 cell clones expanded compatible with the use of these regulatory Tr1 lymphocytes for cell therapy.

TABLE 1

Characterization of ovalbumin-specific Tr1 clones in terms of doubling potential, clonogenicity and telomere length regulation.

| Testing | Conditions | Results |
| --- | --- | --- |
| Maximal Doublings before senescence | | 41.4 ± 4.5 |
| Clonogenicity semi-solid medium | Jurkat cells | 60% confluence after 6 weeks |
| | Tr1 clones | 0% confluence after 6 weeks |
| Clonogenicity in liquid medium | Jurkat cells | 78 growing clones on 3168 seeded wells |
| | Tr1 clones | 1 growing clones on 3456 seeded wells |
| Doubling times (hour/cycle) n = 5 | Before 30 doublings | 76.8 ± 12.7 |
| | Between 30 and 40 doublings | 90.4 ± 12.3 |
| Telomere length (Kb) n = 4 | After 30 doublings | between 2.5 and 20 Kb |
| | After 40 doublings | between 2.5 and 5 Kb |

Figure 7:
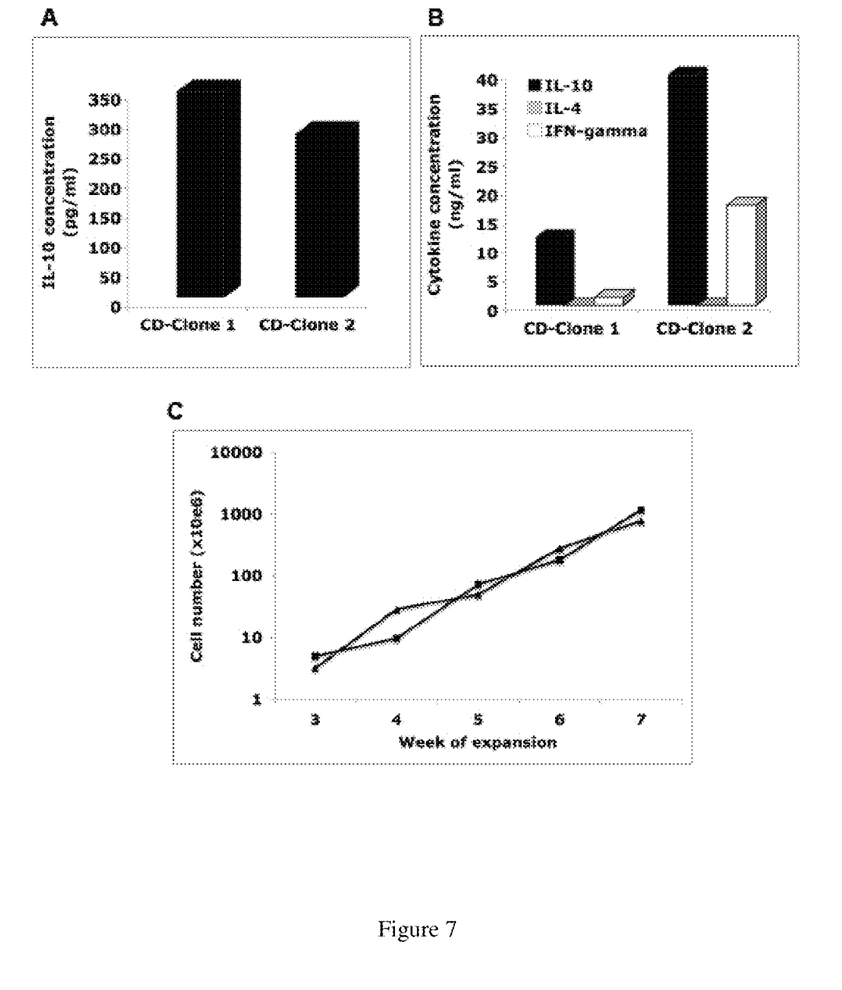
FIG. 7: Cytokine and expansion profiles of ovalbumin specific Tr1 clones from Crohn's disease patients. (A) Tr1 clones were assessed for their specificity to ovalbumin after antigen specific activation during two days in the presence of antigen presenting cells. Ovalbumin-specific production of IL-10 was measured in supernatants by ELISA on three clones given as examples of the quality control testing. Results are expressed as the delta of IL-10 production between stimulating conditions with or without ovalbumin. (B) The Tr1 specific cytokine production profile was evaluated by ELISA on supernatant of anti-CD3+anti-CD28 activated Tr1 clones. (C) Expansion yields of ovalbumin of two Tr1 clones were evaluated by cell count once a week upon weekly stimulation with artificial *drosophila* derived feeder cells.

Finally, in order to demonstrate the feasibility of the manufacturing process with patient's blood cells, ovalbumin specific Tr1 cell clones were successfully produced and expanded up to 1 billion from the PBMCs of Crohn's disease patients (FIG. 7).

In conclusion, we set up a manufacturing process that allow the production of up to 1 billion of ovalbumin-specific Tr1 cell clones for the treatment of severe refractory Crohn's disease patients. We hypothesize that these cells will home to the inflamed gut and will release the inflammatory cytokines after encounter with their specific antigen ovalbumin.

A phase I/IIa clinical trial to test this hypothesis and to evaluate the tolerability of this treatment has started in March 2008 in severe refractory Crohn's disease patient.

An increased number of Crohn's disease patients are refractory to conventional treatment such as non-steroid anti-inflammatory drugs (NSAID, for example Pentasa), corticoids (solupred, prednisolone), immunosuppressants (Azathioprine, Methotrexate) and anti-TNF based medications (Remicade, Humira, Cimzia). These patients can be grouped under the term of Chronic Active Crohn's Disease patients (CACD) because of the persistent inflammatory status of the digestive tract that leads to a degradation in the quality of life and well being. CACD patients display a history of Crohn's disease activity index (CDAI) superior or equal to 220 for at least 6 months.

The Crohn's Disease Activity Index or CDAI is a research tool used to quantify the symptoms of patients with Crohn's disease. This is of importance in research studies done on medications used to treat Crohn's disease; most major studies on newer medications use the CDAI in order to define response or remission of disease. A score of more than 220 identifies a patient with active pathology, a CDAI lower or equal to 150 identifies a patient in remission of the disease.

| CDAI calculator | |
| --- | --- |
| Clinical or laboratory variable | Weighting factor |
| Number of liquid or soft stools each day for seven days | X2 |
| Abdominal pain (graded from 0-3 on severity) each day for seven days | X5 |
| General well being, subjectively assessed from 0 (well) to 4 (terrible) each day for seven days | X7 |
| Presence of complications* | X20 |
| Taking Lomitil or opiates for diarrhea | X30 |
| Presence of an abdominal mass (0 as none, 2 as questionable, 5 as definite) | X10 |
| Absolute deviation of Hematocrit from 47% in men and 42% in women | X6 |
| Percentage deviation from standard weight | X1 |

*Complications: arthralgia, uveitis, erythema nodosum, aphthous ulcers, pyoderma gangrenosum, anal fissure, new fistula, abscess (score 1 per item).

Refractory CACD patients were administrated by intravenous way with Tr1 cell clones specific for the antigen ovalbumin.

Figure 8:
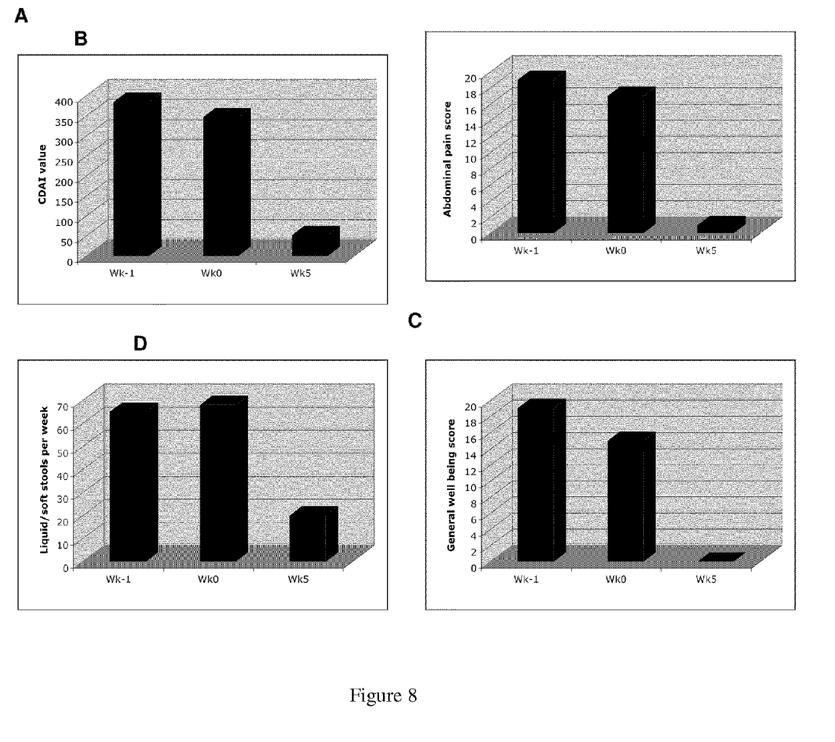

FIG. 8 shows the induction of remission by the decrease in the CDAI (panel A) in a CACD patient 5 weeks after treatment with ovalbumin-specific Tr1 cells. Reduction of CDAI is achieved in part by a diminution of abdominal pain (panel B), number of liquid or soft stools per week (panel C) and general well being score (panel D).

The invention claimed is:

1. A method for treating an intestinal inflammatory condition in a human subject in need thereof, consisting of administering to the subject an effective amount of a composition consisting of at least one human Tr1 cell population directed against a food antigen from common human diet.

2. The method according to claim 1, wherein said intestinal inflammatory condition is an inflammatory bowel disease.

3. The method according to claim 2, wherein said inflammatory bowel disease is Crohn's disease.

4. The method according to claim 2, wherein said inflammatory bowel disease is ulcerative colitis.

5. The method according to claim 1, wherein said intestinal inflammatory condition is an intestinal inflammation linked to food allergy or intolerance.

6. The method according to claim 5, wherein said intestinal inflammation is linked to milk protein allergy.

7. The method according to claim 5, wherein said intestinal inflammation is linked to celiac disease.

8. The method according to claim 5, wherein said intestinal inflammation is linked to hen egg allergy.

9. The method according to claim 5, wherein said intestinal inflammation is linked to peanut allergy.

10. The method according to claim 1, wherein the composition comprises human Tr1 cells autologous to the cells of said subject.

11. The method according to claim 1, wherein $10^4$/kg to $10^9$/kg Tr1 cells are administered to the subject in need thereof.

12. A method for treating an intestinal inflammatory condition in a human subject in need thereof, consisting of administering to the subject an effective amount of a composition consisting of at least one human Tr1 cell population directed against a food antigen from common human diet, and one or more therapeutic agents used for treating an intestinal inflammatory condition.

13. The method according to claim 1, wherein said subject has not responded adequately to one or more therapeutic agents selected from the group consisting of: anti-TNF antibody, natalizumab, anti-IL-1 antibody, anti-IL-6 antibody, anti-IL-12 antibody, anti-IL-17 antibody, anti-IL-23 antibody, IL-1 receptor antagonist analogs, aminosalicyclic acid and analogs, corticoids, probiotics, methotrexate, azathioprine, 6-mercaptopurine, thalidomide, and leflunomide.

14. A process for treating an intestinal inflammatory condition in a human subject in need thereof, comprising:
    obtaining human Tr1 cells directed to a selected food antigen from common human diet, said human Tr1 cells being obtained from a blood sample of said subject,
    cloning said human Tr1 cells directed to a selected food antigen from common human diet,
    further expanding said cloned human Tr1 cells obtained at the previous step, and
    performing the method of claim 1 on the subject.

15. The process according to claim 14, wherein the human Tr1 clones are administered to the subject by an intravenous route.

16. A method for treating an intestinal inflammatory condition in a human subject in need thereof, consisting of administering to the subject an effective amount of a composition comprising at least one human Tr1 cell population directed against a food antigen from common human diet, wherein the composition is administered to the subject not together with or in combination with the food antigen from common human diet.

17. The method according to claim 1, wherein the composition consisting of the at least one human Tr1 cell population is administered to the subject by an intravenous route.

18. The method according to claim 1, wherein the human subject in need thereof suffers from a chronic intestinal inflammatory condition.

19. The method according to claim 1, wherein the human subject in need thereof suffers from a pre-existing intestinal inflammatory condition.

20. The method according to claim 1, wherein said food antigen from common human diet is selected from the group consisting of: ovalbumin, casein, beta-lactoglobulin, soya protein, gliadin, peanuts, and fragments, and mixtures thereof.

* * * * *